United States Patent
Palle et al.

(10) Patent No.: US 10,526,279 B2
(45) Date of Patent: Jan. 7, 2020

(54) PROCESS FOR THE PREPARATION OF TERIFLUNOMIDE

(71) Applicant: BIOCON LIMITED, Bangalore (IN)

(72) Inventors: Venkata Raghavendracharyulu Palle, Hyderabad (IN); Ramakrishna Parameshwar Bhat, Dhareshwar (IN); Mariappan Kaliappan, Nagamalai (IN); Jithendra R. Babu, Aragonda (IN); Rajmahendra Shanmughasamy, Chinnaelasagiri (IN)

(73) Assignee: BIOCON LIMITED, Bangalore (IN)

( * ) Notice: Subject to any disclaimer, the term of this patent is extended or adjusted under 35 U.S.C. 154(b) by 0 days.

(21) Appl. No.: 15/736,981

(22) PCT Filed: Jun. 16, 2016

(86) PCT No.: PCT/IB2016/053556
§ 371 (c)(1),
(2) Date: Dec. 15, 2017

(87) PCT Pub. No.: WO2016/203410
PCT Pub. Date: Dec. 22, 2016

(65) Prior Publication Data
US 2018/0170859 A1    Jun. 21, 2018

(30) Foreign Application Priority Data

Jun. 17, 2015    (IN) ............ 3028/CHE/2015

(51) Int. Cl.
| | | |
|---|---|---|
| C07C 255/23 | (2006.01) | |
| C07C 253/14 | (2006.01) | |
| C07D 261/08 | (2006.01) | |
| C07C 253/00 | (2006.01) | |
| G01N 23/20 | (2018.01) | |
| G01N 25/48 | (2006.01) | |
| G01R 33/46 | (2006.01) | |

(52) U.S. Cl.
CPC .......... C07C 255/23 (2013.01); C07C 253/00 (2013.01); C07C 253/14 (2013.01); C07D 261/08 (2013.01); *G01N 23/20075* (2013.01); *G01N 25/4866* (2013.01); *G01R 33/46* (2013.01)

(58) Field of Classification Search
None
See application file for complete search history.

(56) References Cited

U.S. PATENT DOCUMENTS

| | | |
|---|---|---|
| 5,494,911 A | 2/1996 | Bartlett et al. |
| 5,679,709 A | 10/1997 | Bartlett et al. |

FOREIGN PATENT DOCUMENTS

| | | |
|---|---|---|
| DE | 634286 C | 8/1936 |
| WO | 2001/60363 A1 | 8/2001 |
| WO | 2012/110911 A1 | 8/2012 |
| WO | 2015/029063 A1 | 3/2015 |

OTHER PUBLICATIONS

International Search Report for International Application No. PCT/IB2016/053556 dated Sep. 6, 2016.
Written Opinion of the International Searching Authority for International Application No. PCT/IB2016/053556 dated Sep. 6, 2016.

*Primary Examiner* — Kamal A Saeed
(74) *Attorney, Agent, or Firm* — Katten Muchin Rosenman LLP (57) ABSTRACT

The present invention provides a process for the preparation of Teriflunomide (Formula-I). The present invention describes the synthesis of Teriflunomide without isolating the intermediate Leflunomide. Teriflunomide is prepared from 5-Methyl isoxazole-4-carboxylic acid by converting to its acid chloride and coupling with 4-trifluoromethyl aniline to obtain Leflunomide (which is not isolated) followed by ring opening reaction using aq. Sodium Hydroxide to form Teriflunomide. In other words, the process is telescoped from 5-methylisoxazole-4-carbonyl chloride.

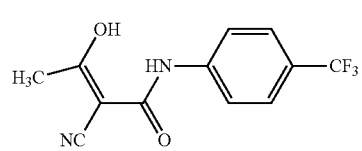

Formula-I

19 Claims, 7 Drawing Sheets

| # | RT | Area | Area % | Main Peak Height |
|---|---|---|---|---|
| 1 | 6.996 | 25.475 | 0.045 | 1.820 |
| 2 | 21.451 | 8.417 | 0.015 | 0.390 |
| 3 | 23.187 | 56176.066 | 99.940 | 1974.461 |

PROCESS FOR THE PREPARATION OF TERIFLUNOMIDE

TECHNICAL FIELD OF THE INVENTION

The present invention relates to a novel process for the preparation of Teriflunomide represented by the structural Formula-I, Formula-I Teriflunomide (AUBAGIO™) is an oral de novo pyrimidine synthesis inhibitor of the DHO-DH enzyme, with the chemical name (Z)-2-Cyano-3-hydroxy-but-2-enoicacid-(-4-trifluoromethylphenyl)-amide.

BACKGROUND OF THE INVENTION

Teriflunomide, an immunomodulatory agent with anti-inflammatory properties, inhibits dihydroorotate dehydrogenase, a mitochondrial enzyme involved in de novo pyrimidine synthesis. The exact mechanism by which Teriflunomide exerts its therapeutic effect in multiple sclerosis is unknown but may involve a reduction in the number of activated lymphocytes in CNS.

U.S. Pat. No. 5,679,709 claims Teriflunomide and its pharmaceutically acceptable salts, composition and a method of treating auto immune diseases.

U.S. Pat. No. 5,494,911 discloses the synthesis of Teriflunomide, coupling of 5-methyl isoxazole-4-carbonyl chloride with 4-(Trifluoromethyl) aniline in acetonitrile solvent to obtain Leflunomide. Subsequent ring opening reaction using a base followed by acidification results in Teriflunomide. Synthesis is shown in the Scheme-1.

Scheme-1:

This method has the disadvantages of usage of acetonitrile in the coupling which involves the necessity to isolate the Leflunomide.

PCT publication WO2015/029063 claims the process for preparation of Teriflunomide by reacting 5-Methyl isoxazole-4-carboxylic acid with thionyl chloride using mixed solvents and converting to Leflunomide in-situ by reacting with 4-(Trifluoromethyl) aniline, reacting Leflunomide with a base followed by acidification. Synthesis is depicted in the scheme-2.

Scheme-2:

PCT Publication WO 2001/60363 mentions about the usage of biphasic medium for the synthesis of Leflunomide. However, the usage of organic solvent especially toluene leads to the isolation issue due to the phase separation problem. Usage of Dimethyl acetamide is undesirable and improved processes which avoid its use are required.

Presently known methods have several disadvantages, including:

(i) Usage of mixed solvents (involving a solvent with higher boiling point) in the preparation of acid chloride. Distillation of the solvent may lead to loss of the product as the boiling point of acid chloride is very close to the boiling point of DMF. In other words, this operation is highly dependent on the vacuum/temperature applied for the removal.

(ii) Laborious work up procedure for the isolation of Leflunomide.

(iii) Purification involves a solvent with higher boiling point which is not desirable.

(iv) Overall yield is often low (~50%).

Reported procedures involving Leflunomide as the intermediate, involve isolation of the Leflunomide as a solid in one or the other way. The isolation involves concentration of the volatile solvents in presence of base leading to the formation of impurities (DE 634286).

Accordingly, there is a need for safe, simple and efficient method for producing Teriflunomide, that not only avoid isolation steps, but also affords product of required quality and without undesired impurity. It is therefore, needed to develop a process which not only overcomes the disadvantages of prior art but also is economical, operationally simple and industrially applicable.

The present invention provides an improved method for production of Teriflunomide by eliminating the steps of isolation of Leflunomide intermediate. In other words, the process of the present invention involves telescoping from 5-methylisoxazole-4-carbonyl chloride to the crude Teriflunomide of Formula-I.

OBJECTS OF THE INVENTION

It is an object of the present invention to provide an improved process for the production of Teriflunomide in higher yields and purity.

It is an object of the present invention to provide a safe, simpler and economical process for the preparation of Teriflunomide

It is another object of the present invention to provide a commercially useful process for the preparation of Teriflunomide by eliminating the steps of isolation of Leflunomide intermediate.

It is yet another object of the present invention to provide a product with high yield and high chemical purity.

It is yet another object of the present invention to provide pure crystalline Teriflunomide.

SUMMARY OF THE INVENTION

According to an aspect of the present invention, there is provided a process for the preparation of (Z)-2-cyano-3-hydroxy-but-2-enoic acid-(4-trifluoro methylphenyl)-amide of formula-I, (I)

comprising the steps of:
a) converting 5-methylisoxazole-4-carboxylic acid of formula-V (V)

to 5-methylisoxazole-4-carbonyl chloride of formula-IV (IV)

using a chlorinating agent;

b) reacting the compound of formula-IV with 4-(trifluoromethyl)aniline of formula-III (III)

in a biphasic medium in the presence of an inorganic base to afford N-(4'-trifluoromethylphenyl)-5-methylisoxazole-4-carboxamide of formula-II;

(II)

c) reacting the compound of formula-II with aqueous sodium hydroxide in a mixture of solvents to provide (Z)-2-cyano-3-hydroxy-but-2-enoic acid-(4-trifluoromethyl phenyl)-amide of formula-I;

d) optionally, purifying the compound of formula-I from a mixture of solvents to provide pure crystalline (Z)-2-cyano-3-hydroxy-but-2-enoic acid-(4-trifluoromethyl phenyl)-amide compound of formula-I.

According to another aspect of the present invention there is provided a process for the preparation of (Z)-2-cyano-3-hydroxy-but-2-enoic acid-(4-trifluoro methylphenyl)-amide of formula-I, (I)

comprising the steps of:
a) converting 5-methylisoxazole-4-carboxylic acid of formula-V (V)

to 5-methylisoxazole-4-carbonyl chloride of formula-IV (IV)

using a chlorinating agent with an aromatic hydrocarbon solvent b) reacting the compound of formula-IV with 4-(trifluoromethyl) aniline of formula-III (III)

in a biphasic medium in the presence of an inorganic base to afford N-(4'-trifluoromethylphenyl)-5-methylisoxazole-4-carboxamide of formula-II, (II)

c) reacting the compound of formula-II with aqueous sodium hydroxide in a mixture of solvents to provide (Z)-2-cyano-3-hydroxy-but-2-enoic acid-(4-trifluoromethyl phenyl)-amide of formula-I, wherein step c) reaction is carried on without isolating compound of Formula II d) optionally, purifying the compound of formula-I from a mixture of solvents to provide pure crystalline (Z)-2-cyano-3-hydroxy-but-2-enoic acid-(4-trifluoromethyl phenyl)-amide of formula-I

According to yet another aspect of the present invention there is provided a process for the preparation of (Z)-2-cyano-3-hydroxy-but-2-enoic acid-(4-trifluoro methylphenyl)-amide of formula-I (I)

comprising the steps of:
a) converting 5-methylisoxazole-4-carboxylic acid of formula-V (V)

to 5-methylisoxazole-4-carbonyl chloride of formula-IV (IV)

using thionyl chloride in toluene
b) reacting the compound of formula-IV with 4-(trifluoromethyl) aniline of formula-III (III)

in ethyl methyl ketone and water in the presence of cesium carbonate to afford N-(4'-trifluoromethylphenyl)-5-methylisoxazole-4-carboxamide of formula-II, (II)

c) reacting the compound of formula-II with aqueous sodium hydroxide in a mixture of solvents to provide (Z)-2-cyano-3-hydroxy-but-2-enoic acid-(4-trifluoromethyl phenyl)-amide of formula-I, wherein step c) reaction is carried on without isolating compound of Formula II d) optionally, purifying the compound of formula-I from a mixture of acetonitrile and water to provide pure crystalline (Z)-2-cyano-3-hydroxy-but-2-enoic acid-(4-trifluoromethyl phenyl)-amide of formula-I.

DETAILED DESCRIPTION OF THE INVENTION

The present invention describes the synthesis of Teriflunomide (Formula I) without isolating the intermediate Leflunomide. In the present invention, Teriflunomide is prepared from 5-Methyl isoxazole-4-carboxylic acid by converting to its acid chloride and coupling with 4-trifluoromethyl aniline to obtain Leflunomide (which is not isolated) followed by ring opening reaction using aq. NaOH. The process is telescoped from 5-methylisoxazole-4-carbonyl chloride.

Each step of the process disclosed herein are contemplated both in the context of the multistep sequences described and individually Synthetic Scheme of the Present Invention:

The present invention eliminates the need for the isolation of the Leflunomide (Formula II) intermediate which is a time consuming process and often leads to impurities in the product mixture. In other words, the process involves telescoping from 5-methylisoxazole-4-carbonyl chloride to the crude(Z)-2-cyano-3-hydroxy-but-2-enoic acid-(4-trifluoromethyl phenyl)-amide of Formula-I (Teriflunomide), with significant advantageous over the known processes.

The process offers several advantages over the known processes including:
   Usage of desired stoichiometric equivalents of 4-(Trifluoromethyl) aniline in comparison of excess equivalents as mentioned in prior art.
   Elimination of the need to isolate Leflunomide.
   Usage of cheaper solvents.
   Solid base which is water soluble.
   Ease of handling Accordingly, present invention provides a process of preparation of (Z)-2-cyano-3-hydroxy-but-2-enoic acid-(4-trifluoromethyl phenyl)-amide (Formula-I) Teriflunomide comprising steps of
   i. Converting 5-Methyl isoxazole-4-carboxylic acid (Formula-V) to 5-methylisoxazole-4-carbonyl chloride (Formula-IV) using thionyl chloride and optionally a solvent.
   ii. Coupling of Formula-IV with Formula-III in the presence of a base and a biphasic medium to form Leflunomide (Formula-II). The base may be an organic base like Triethylamine, 4-(Trifluoromethyl) aniline or an inorganic base consisting of NaOH or Cesium carbonate. Biphasic medium consists of an organic solvent and water. Organic solvent may be chosen from Methyl isobutyl ketone. Ethyl acetate and Isopropyl acetate, preferably Methyl ethyl ketone. Further, the process involves the usage of desired stoichiometry of Formula-III.

iii. Converting Leflunomide of Formula-II to (Z)-2-cyano-3-hydroxy-but-2-enoic acid-(4-trifluoromethyl phenyl)-amide of Formula-I using a base and solvent mixtures. The solvent mixture comprises of water, alcohol preferably methanol and an organic solvent preferably Methyl ethyl ketone. Base comprises of metal carbonates or hydroxides. Further, the base could be chosen from Cesium carbonate, sodium carbonate, potassium carbonate or sodium hydroxide, preferably Cesium carbonate.

iv. Purifying the crude (Z)-2-cyano-3-hydroxy-but-2-enoic acid-(4-trifluoromethyl phenyl)-amide of Formula-I using a mixture of water and an organic solvent to obtain pure (Z)-2-cyano-3-hydroxy-but-2-enoic acid-(4-trifluoromethyl phenyl)-amide Formula-I, Teriflunomide. The organic solvent could be an alcohol or a nitrile preferably methanol, more preferably acetonitrile. The purification process has been designed to limit the Formula-III as an impurity below a specific limit.

Evaporation of excess thionyl chloride occurs faster when the reaction was performed in an inert solvent compared to neat conditions. The solvent could be an aromatic hydrocarbon, selected from toluene, benzene or xylene; preferably toluene.

In an embodiment of the present invention the chlorinating agent is selected from thionyl chloride, oxalyl chloride, phosphorous oxychloride and phosphorous pentachloride; preferably thionyl chloride.

In another embodiment of the present invention the inorganic base is selected from sodium carbonate, potassium carbonate, sodium hydroxide and cesium carbonate; preferably cesium carbonate.

In another embodiment of the present invention the biphasic medium used in step b) is selected from ethyl acetate, ethyl methyl ketone, methyl isobutyl ketone, 2-methyl tetrahydrofuran and water.

In yet another embodiment of the present invention the mixture of solvents used in step c) is selected from methyl ethyl ketone, methanol, methyl isobutyl ketone, 2-methyl tetrahydrofuran, ethyl acetate and water.

In yet another embodiment of the present invention the solvent used for purifying the compound of formula I is selected from acetonitrile-water, methanol-water and ethanol-water According to a preferred embodiment of the present invention there provided a process for preparation of pure crystalline form of Teriflunomide (Formula I).

Few advantages of this invention includes and not necessarily restricted to,

Usage of Cesium carbonate: Cesium carbonate is easy to handle, commercially available, readily soluble in water and thereby easy to remove from the product. Residual acidic impurities react readily with Cesium carbonate to form water soluble products. Cesium carbonate is a mild base which induces required basicity into the reaction medium.

Usage of Biphasic Medium:

Usage of organic solvent alone leads to the degradation of Leflunomide during reaction. Moreover, process is not 'scale up' friendly due to the vigorous liberation of carbon dioxide.

Usage of water alone leads to the decomposition of acid chloride resulting in lower yield of product.

Usage of biphasic medium facilitates the easy removal of the by-product as soon as it is formed. This indirectly, increases the rate of reaction and yield and quality of product.

The absence of base along with the product prevents the degradation during unit operations.

Usage of Methyl Ethyl Ketone:

Economical in comparison to the conventional acetonitrile.

Commercially available.

Methyl ethyl ketone is inert under the reaction conditions.

Less volatile and less viscous and thereby easy to handle in the scale up.

Class-III solvent.

Product is readily soluble in the solvent and thereby reaction volume is relatively less. Usage of solvents like DCM, toluene in which the product is less soluble, the product precipitates out thereby necessitating the operations like decantation, concentration or filtration.

Downstream process may not involve concentration of the solvent as it is miscible with water and methanol (solvents in the subsequent step).

Presence of the solvent in the subsequent step facilities the reaction due to the solubility of sodium salt of API. In other words, concentration of the solvent is not a necessary criteria.

Also, the presence of the solvent helps in the isolation of the product by avoiding the formation of lumps of the product. In other words, the product can be easily filtered. On the contrary, usage of similar solvents like MIBK result formation of lumps.

Solution of Leflunomide in Methyl ethyl ketone is stable.

Controlling Formula-III: Another advantage of the process is controlling the Formula-III to a specified limit. Reported procedures involve usage of excess stoichiometry of formula-III for the coupling reaction. This was necessary as formula-III was used as base and reactant. However, in the current process a desired stoichiometry of formula-III was used for coupling as inorganic base was serving the purpose. The process developed is capable of controlling the Formula-III as an impurity below 0.15%. Further, the process is capable of controlling the Formula-III as an impurity below 100 ppm. Further, the process is capable of controlling the Formula-III as an impurity below 32 ppm.

The scheme is represented by following examples. These examples are for illustration only and hence should not be construed as limitation of the scope of invention.

Example 1: Preparation of
5-Methylisoxazole-4-carbonyl chloride
[Formula-IV]

A round bottomed flask equipped with a mechanical stirrer, condenser, thermometer pocket and a stopper were added 5-Methylisoxazole-4-carboxylic acid [Formula-V] (75.0 g, 0.59 mol) and Toluene (225 mL). The slurry was added with Thionyl chloride (140.41 g, 1.18 mol) and the reaction mixture was gradually heated to 75±5° C. and stirred at same temperature for 10-12 h. The progress of the reaction was monitored by HPLC (Acid chloride was analyzed as corresponding methyl ester by quenching the sample in methanol). After the completion of reaction, the reaction mixture was concentrated under reduced pressure at 55±5° C. to afford 5-Methylisoxazole-4-carbonyl chloride of Formula-IV as a liquid.

Example 1A: Preparation of 5-Methylisoxazole-4-carbonyl chloride [Formula-IV]

A round bottomed flask equipped with a mechanical stirrer, condenser, thermometer pocket and a stopper were added 5-Methylisoxazole-4-carboxylic acid (3.00 g, 0.02 mol) and Thionyl chloride (14.66 g, 0.12 mol) and the reaction mixture was gradually heated to 45±5° C. and stirred at same temperature for 2 to 3 h. The progress of the reaction was monitored by TLC (Acid chloride was analyzed as corresponding methyl ester by quenching the sample in methanol). After the completion of reaction, the reaction mixture was concentrated under reduced pressure at 45±5° C. to afford 5-Methylisoxazole-4-carbonyl chloride as a liquid (0.59 mol).

Example 2: Preparation of 5-Methyl-N-[4-(trifluoromethyl)phenyl]isoxazole-4-carboxamide (Leflunomide) [Formula-II]

A round bottom flask equipped with a mechanical stirrer, a condenser, a temperature indicator and an additional funnel was charged with 4-(Trifluoromethyl) aniline [Formula-III] (95.08 g, 0.59 mol), Ethyl methyl ketone (150 mL), Cesium carbonate (144.19 g, 0.44 mol) and water (150 mL). The reaction mixture was heated to 45±2° C. A solution of 5-Methylisoxazole-4-carbonyl chloride [Formula-IV] (from Example-1) in Ethyl methyl ketone (75.0 mL) was slowly added into the reaction mixture at 55±10° C. and stirred for 1 h. Progress of the reaction was monitored by HPLC. After completion of the reaction, the resultant reaction mixture was cooled to room temperature and the layers were separated. The organic (ethyl methyl ketone) layer containing 5-Methyl-N-[4-(trifluoromethyl) phenyl] isoxazole-4-carboxamide (Leflunomide) [Formula-II] was taken to the ring opening without isolation.

Example 3: Preparation of 5-Methyl-N-[4-(trifluoromethyl)phenyl]isoxazole-4-carboxamide (Leflunomide) [Formula-II]

A round bottom flask equipped with a mechanical stirrer, a condenser, a temperature indicator and an additional funnel was charged with 4-(Trifluoromethyl) aniline [Formula-III] (3.80 g, 0.023 mol), Ethyl acetate (12.0 mL), Cesium carbonate (7.69 g, 0.023 mol), water (9.00 mL) and the reaction mixture was heated to 40±2° C. A solution of 5-Methylisoxazole-4-carbonyl chloride [Formula-IV] (0.023 mol) in Ethyl acetate (6.00 mL) was slowly added into the reaction mixture at 45±5° C. and stirred for 1 h. Progress of the reaction was monitored by HPLC. After the completion of reaction, the resultant reaction mixture containing 5-Methyl-N-[4-(Trifluoromethyl) phenyl] isoxazole-4-carboxamide (Leflunomide) [Formula-II] was taken forward to the ring opening without isolation.

Example 4: Preparation of 5-Methyl-N-[4-(trifluoromethyl)phenyl]isoxazole-4-carboxamide (Leflunomide) [Formula-II]

A round bottom flask equipped with a mechanical stirrer, a condenser, a temperature indicator and an additional funnel was charged with 4-(Trifluoromethyl) aniline [Formula-III] (6.34 g, 0.039 mol), ethyl methyl ketone (10.0 mL), sodium hydroxide (1.57 g, 0.039 mol) and water (10.0 mL) and the reaction mixture was heated to 45±5° C. A solution of 5-Methylisoxazole-4-carbonyl chloride [Formula-IV] (0.039 mol) in ethyl methyl ketone (5.00 mL) was slowly added into the reaction mixture maintaining the same temperature and stirred for 1 h. Progress of the reaction was monitored by HPLC. After the completion of reaction, the resultant reaction mixture was cooled between 25° C. and 30° C. and layers were separated. The organic (Ethyl methyl ketone) layer containing 5-methyl-N-[4-(trifluoromethyl) phenyl] isoxazole-4-carboxamide (Leflunomide) [Formula-II] was taken forward to the ring opening without isolation.

Example 5: Preparation of (Z)-2-cyano-3-hydroxy-N-[4-(trifluoromethyl)phenyl] but-2-enamide (Crude Teriflunomide) [Formula-I]

A round bottom flask equipped with a mechanical stirrer, a condenser, a temperature indicator and an additional funnel was charged with organic (Ethyl methyl ketone) layer containing 5-methyl-N-[4-(trifluoromethyl) phenyl] isoxazole-4-carboxamide (Leflunomide) [Formula-II] (from Example-2). Methanol (150 mL) was added and the reaction mixture was heated to 45±2° C. A solution of sodium hydroxide (30.69 g, 0.76 mol) in water (150 mL) was added slowly and the reaction mixture was stirred at 55±5° C. for 1 h. Progress of the reaction was monitored by HPLC. After the completion of reaction, the reaction mixture was treated with a charcoal slurry (15.0 g, 20% w/w with respect to 5-Methyl isoxazole-4-carboxylic acid) in water (300 mL) at 55±5° C. for 1 h. The reaction mixture was cooled between 25° C. and 30° C., filtered through Celite® bed and washed the bed with water (300 mL). The filtrate was acidified with 5N HCl and stirred for 1 h. The solid was filtered and washed with water (300 mL). The wet cake was taken in a flask and stirred with water (750 mL), filtered and washed with water (300 mL). The wet cake was dried at 60±5° C. under reduced pressure for 20 h to obtain (Z)-2-cyano-3-hydroxy-N-[4-(trifluoromethyl) phenyl] but-2-enamide (crude Teriflunomide) [Formula-I] as a solid (140 g, 87.8% yield, 99.36% AUC).

Example 6: Preparation of (Z)-2-cyano-3-hydroxy-N-[4-(trifluoromethyl)phenyl] but-2-enamide (Crude Teriflunomide) [Formula-I]

A round bottom flask equipped with a mechanical stirrer, a condenser, a temperature indicator and an additional funnel was charged with the reaction mixture (from Example-3) containing 5-Methyl-N-[4-(trifluoromethyl) phenyl] isoxazole-4-carboxamide (Leflunomide) [Formula-II] solution in Ethyl acetate. A solution of sodium hydroxide (1.23 g, 0.030 mol) in water (12.0 mL) was added slowly into the reaction mixture. Methanol (12.0 mL) was added and the reaction mixture was heated to 50±5° C. and the mixture was stirred at the same temperature for 1 h. Progress of the reaction was monitored by HPLC. Diluted the reaction mass with water (30.0 mL) The reaction mass was acidified using 2N HCl solution at 25±5° C. and stirred for 1 h. The solid was filtered, washed with water (12.0 mL). The wet cake was dried at 55±2° C. under reduced pressure for 15 h to obtain (Z)-2-cyano-3-hydroxy-N-[4-(trifluoromethyl) phenyl] but-2-enamide (Crude Teriflunomide) [Formula-I] as a solid (5.75 g, 90.15% yield, 99.42% AUC).

Example 7: Preparation of (Z)-2-cyano-3-hydroxy-N-[4-(trifluoromethyl)phenyl]but-2-enamide (Crude Teriflunomide) [Formula-I]

A round bottom flask equipped with a mechanical stirrer, a condenser, a temperature indicator and an additional funnel was charged with organic layer (from Example-4) containing 5-Methyl-N-[4-(trifluoromethyl) phenyl] isoxazole-4-carboxamide (Leflunomide) [Formula-II] solution in ethyl methyl ketone. Methanol (10.0 mL) was added and the reaction mixture was heated to 50±5° C. A solution of sodium hydroxide (1.57 g, 0.039 mol) in water (10.0 mL) was added slowly into the reaction mixture and the mixture was stirred at the same temperature for 1 h. Progress of the reaction was monitored by HPLC. Diluted the reaction mass with water (10.0 mL) and Ethyl methyl ketone (10 mL). The reaction mass was acidified using 5N HCl solution at 25±5° C. and stirred for 1 h. The solid was filtered, washed with water (20.0 mL). The wet cake was dried at 55±2° C. under reduced pressure for 15 h to obtain (Z)-2-cyano-3-hydroxy-N-[4-(trifluoromethyl) phenyl] but-2-enamide (Crude Teriflunomide) [Formula-I] as a solid (10.0 g, 94.0% yield, 99.38% AUC).

Example 8: Purification of Teriflunomide i. A round bottom flask equipped with a mechanical stirrer, a condenser, a temperature indicator was charged with Crude Teriflunomide [Formula-I] (90.0 g, 0.33 mol, 99.12% AUC), Methanol (2250 mL) and water (180 mL). The reaction mixture was heated to 62±2° C. and maintained at the same temperature for 1 to 2 h. The resulted slurry was cooled between 25° C. and 30° C. and stirred for 1 h. It was filtered, washed the wet solid with Methanol (180 mL). The wet cake was dried at 60±2° C. under reduced pressure for 15 h to obtain pure crystalline Teriflunomide [Formula-I] (78.7 g, 87.44% recovery, >99.9% AUC)

ii. A round bottom flask equipped with a mechanical stirrer, a condenser, a temperature indicator was charged with crude Teriflunomide [Formula-I] (232.5 g, 0.86 mol), Methanol (3022.5 mL) and water (465 mL). The reaction mixture was heated to 65±2° C. and maintained at the same temperature for 1 to 2 h. The resulted slurry was cooled between 25 and 30° C. and stirred for 2 to 3 h. It was filtered, washed the wet solid with Methanol (465 mL). The wet cake was dried at 55±5° C. under reduced pressure for 15 h to obtain pure crystalline Teriflunomide [Formula-I] (210 g, 90.0% recovery, >99.8% AUC).

Example 9: Purification of Teriflunomide

A round bottom flask equipped with a mechanical stirrer, a condenser, a temperature indicator and an additional funnel was charged with crude Teriflunomide [Formula-I] (140 g, 0.52 mol, from Example-5) and acetonitrile (1820 mL) and water (280 mL). The slurry was heated to 65±5° C. and stirred for 1 to 2 h. The resultant slurry was cooled to 25±5° C. and maintained at the same temperature for 2 to 3 h. The slurry was filtered, washed the wet solid with acetonitrile (280 mL). The wet cake was dried at 60±5° C. under reduced pressure for 15 h to afford pure compound (Z)-2-cyano-3-hydroxy-but-2-enoic acid-(4-trifluoro methylphenyl)-amide Teriflunomide [Formula-I] (125.2 g, 89.46% recovery, >99.9% AUC. Content of Formula-III in formula-I was found to be less than 32 ppm.

Example 10: Preparation of Teriflunomide

To a stirred slurry of 5-Methylisoxazole-4-carboxylic acid (1.00 kg, 7.86 mol) in Toluene (3.00 L) was added Thionyl chloride (~2.34 kg, 19.67 mol) and the reaction mixture was gradually heated to 75±5° C. and stirred at same temperature for 10-12 h. After the completion of reaction, the reaction mixture was concentrated under reduced pressure at 55±5° C. to afford 5-Methylisoxazole-4-carbonyl chloride as a liquid.

A mixture of 4-(Trifluoromethyl) aniline (1.27 kg, 7.86 mol), Ethyl methyl ketone (2.00 L), Cesium carbonate (1.92 kg, 5.89 mol) and water (2.00 L) was heated to 55±5° C. A solution of 5-Methylisoxazole-4-carbonyl chloride (7.86 mol) in Ethyl methyl ketone (1.00 L) was slowly added into the reaction mixture at the same temperature and stirred for 1 h. After completion of the reaction, the resultant reaction mixture was cooled to room temperature and the layers were separated. The organic (ethyl methyl ketone) layer containing 5-methyl-N-[4-(trifluoromethyl) phenyl] isoxazole-4-carboxamide (Leflunomide) was taken to the next step without isolation.

To the organic (Ethyl methyl ketone) layer containing 5-methyl-N-[4-(trifluoromethyl) phenyl] isoxazole-4-carboxamide (Leflunomide) (7.86 mol), Methanol (2.00 L) was added and the reaction mixture was heated to 55±5° C. A solution of sodium hydroxide (0.41 kg, 10.25 mol) in water (2.00 L) was added slowly and the reaction mixture was stirred at the same temperature for 1 h. After the completion of reaction, the reaction mixture was treated with a charcoal slurry (0.20 kg, 20% w/w wrt 5-Methyl isoxazole-4-carboxylic acid) in water (4.00 L) at 55±5° C. for 1 h. The reaction mixture was cooled, filtered through Celite® bed and washed the bed with water (4.00 L). The filtrate was acidified with 5N HCl and stirred. The solid was filtered and washed with water (4.00 L). The wet cake was stirred with water (10.0 L), filtered and washed with water (4.00 L). The wet cake was dried at 60±5° C. under reduced pressure to obtain (Z)-2-cyano-3-hydroxy-N-[4-(trifluoromethyl) phenyl] but-2-enamide (crude Teriflunomide) as a solid (1.81 kg, 85.15% yield).

Crude Teriflunomide (1.81 kg, 6.70 mol) was slurried with acetonitrile (23.53 L) and water (36.2 L). The slurry was heated to 65±5° C. and stirred. The slurry was subsequently cooled to room temperature and stirred. The slurry was filtered, washed the wet solid with acetonitrile (36.2 L). The wet cake was dried at 60±5° C. under reduced pressure to afford pure Teriflunomide (1.63 kg, 90.05% recovery, >99.9% AUC). Content of 4-(Trifluoromethyl)aniline (Compound of formula III) is <32 ppm. Overall yield of Teriflunomide based on 5-Methylisoxazole-4-carboxylic acid is 76.68%.

Figure 1:
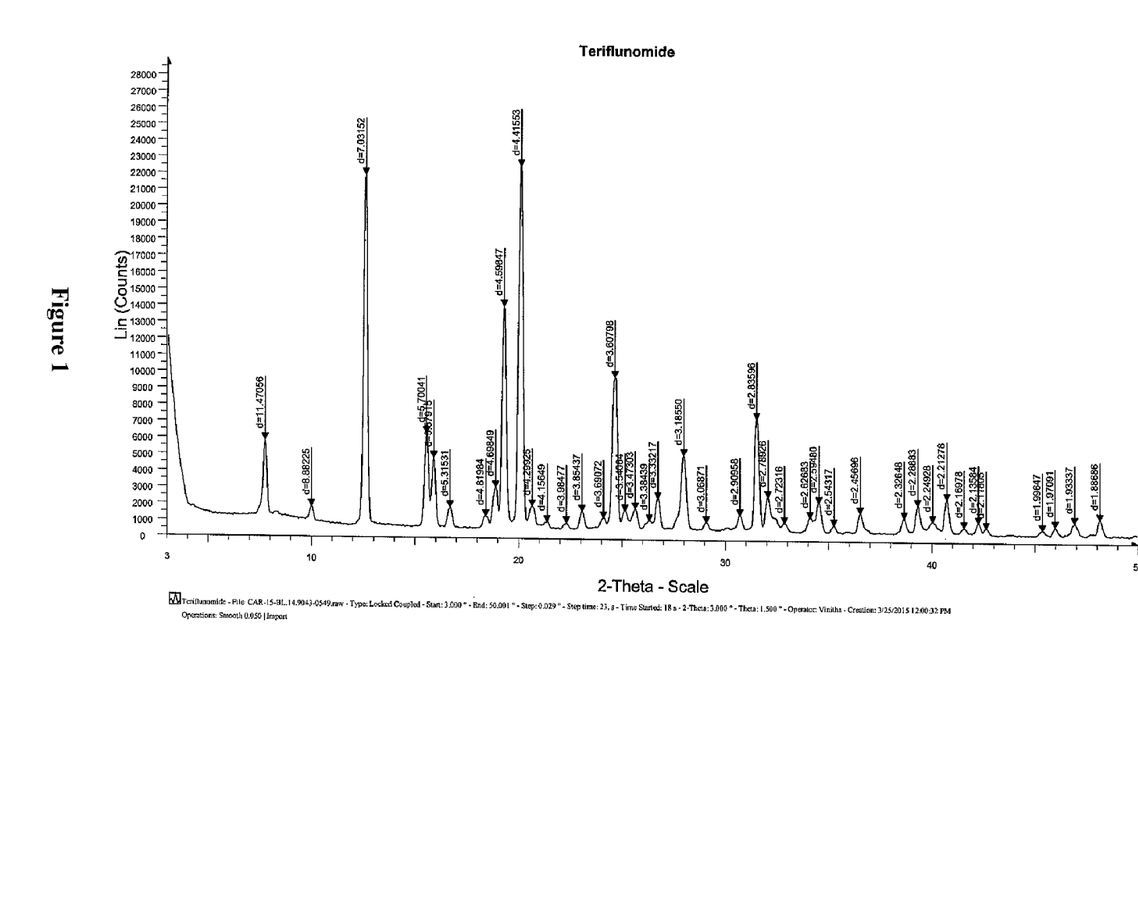
FIG. 1: Illustrates the PXRD pattern of crystalline form of (Z)-2-Cyano-3-hydroxy-but-2-enoicacid-(-4-trifluoromethylphenyl)-amide.

The PXRD pattern of crystalline (Z)-2-Cyano-3-hydroxy-but-2-enoicacid-(-4-trifluoromethylphenyl)-amide is shown in FIG. 1.

Figure 2:
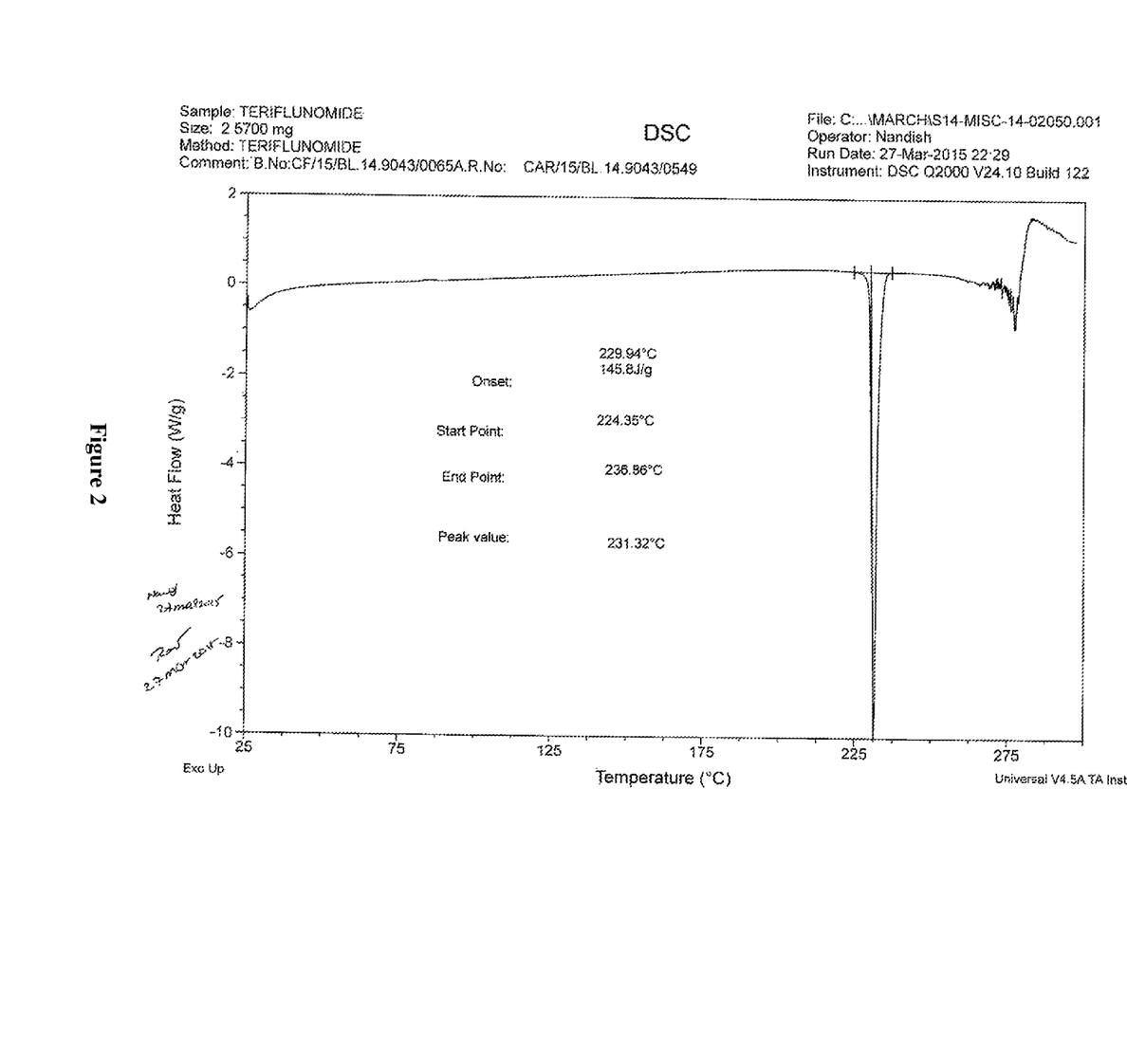
FIG. 2: Illustrates the DSC thermogram of crystalline form of (Z)-2-Cyano-3-hydroxy-but-2-enoicacid-(-4-trifluoromethylphenyl)-amide.

The DSC thermogram of crystalline (Z)-2-Cyano-3-hydroxy-but-2-enoicacid-(-4-trifluoromethylphenyl)-amide is shown in FIG. 2.

Figure 3:
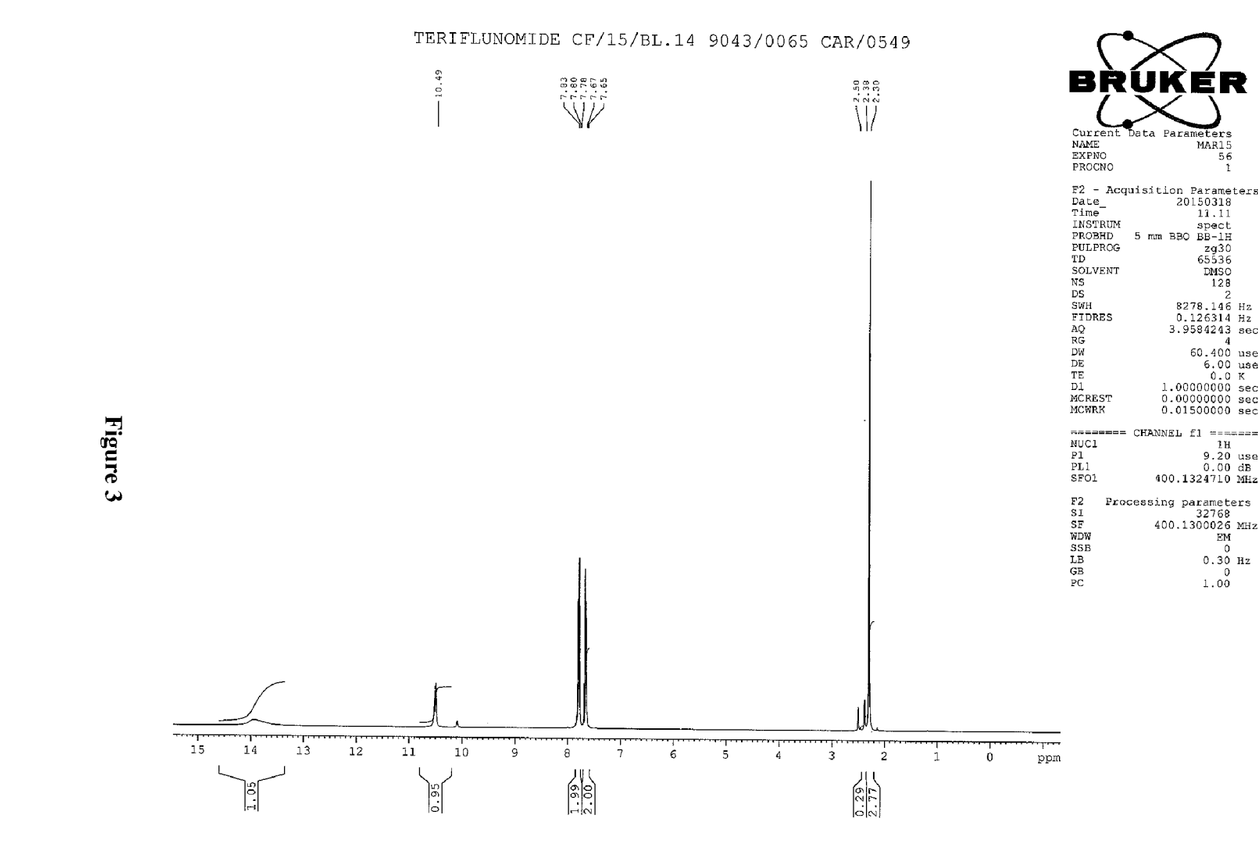
FIG. 3: Illustrates the $^1$HNMR of crystalline form of (Z)-2-Cyano-3-hydroxy-but-2-enoicacid-(-4-trifluoromethylphenyl)-amide.

$^1$H NMR (DMSO-$d_6$, 400 MHz): δ 14.0-13.9 (bs, 1H), 10.50-10.40 (s, 1H), 7.85-7.75 (d, 2H), 7.70-7.60 (d, 2H), 2.5-2.2 (s, 3H). The $^1$HNMR of crystalline form of (Z)-2-Cyano-3-hydroxy-but-2-enoicacid-(-4-trifluoromethylphenyl)-amide is shown in FIG.-3.

Figure 4:
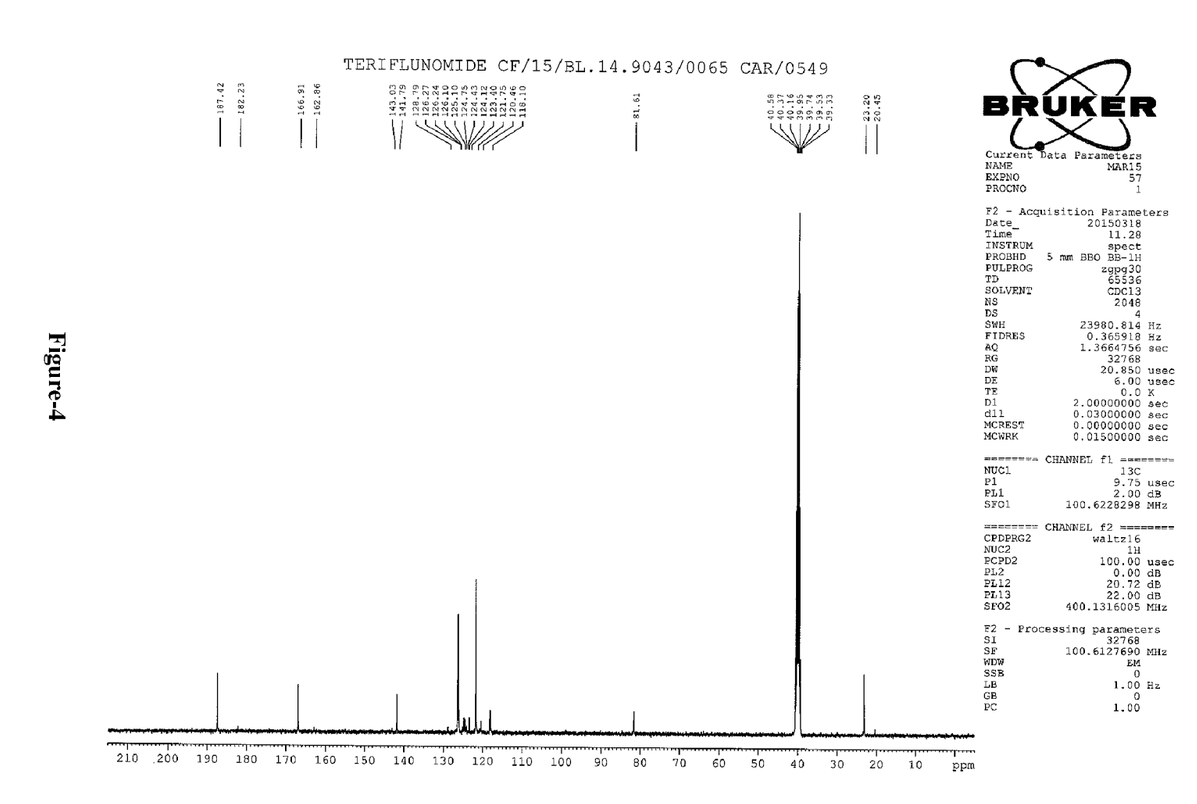
FIG. 4: Illustrates the $^{13}$CNMR of crystalline form of (Z)-2-Cyano-3-hydroxy-but-2-enoicacid-(-4-trifluoromethylphenyl)-amide.
Figure 5:
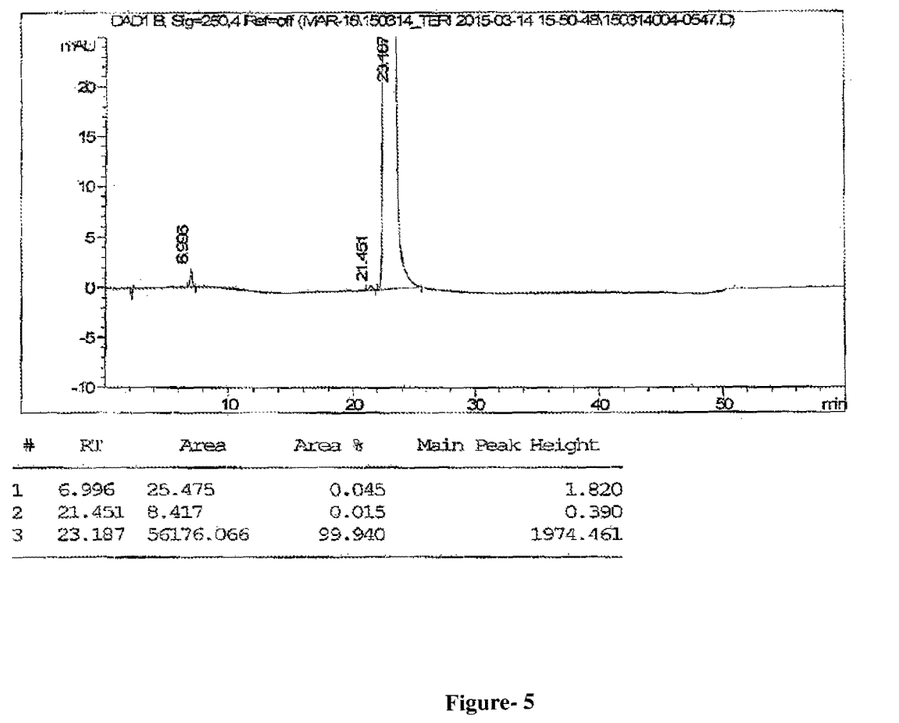
FIG. 5: Illustrates the HPLC of crystalline form of (Z)-2-Cyano-3-hydroxy-but-2-enoicacid-(-4-trifluoromethylphenyl)-amide.

$^{13}$C NMR (DMSO-d$_6$, 100 MHz): δ 187.42, 166.91, 141.79, 126.24, 123.40, 121.75, 120.46, 118.10, 81.61, 23.20. The $^{13}$CNMR of crystalline form of (Z)-2-Cyano-3-hydroxy-but-2-enoicacid-(-4-trifluoromethylphenyl)-amide is shown in FIG. 4

Figure 6:
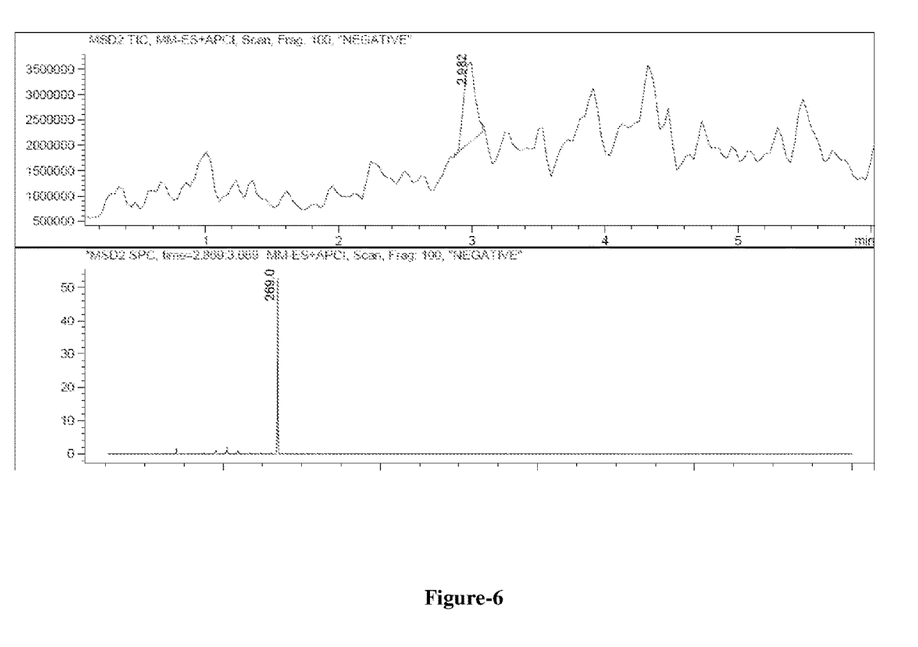
FIG. 6: Illustrates the LCMS of crystalline form of (Z)-2-Cyano-3-hydroxy-but-2-enoicacid-(-4-trifluoromethylphenyl)-amide.

MS: 269.0 (M$^+$−1). The LCMS of crystalline form of (Z)-2-Cyano-3-hydroxy-but-2-enoicacid-(-4-trifluoromethylphenyl)-amide is shown in FIG. 6.

Figure 7:
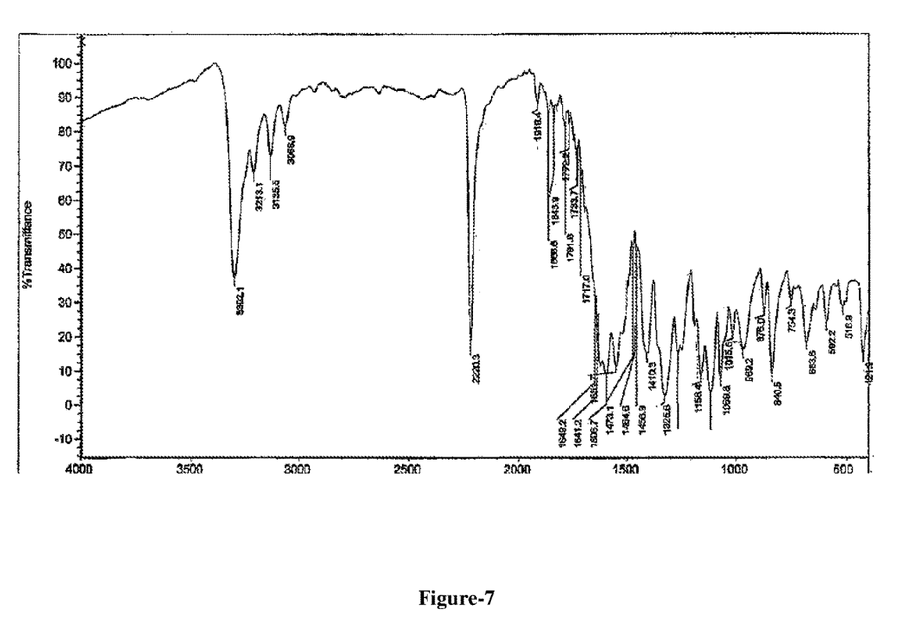
FIG. 7: Illustrates the IR of crystalline form of (Z)-2-Cyano-3-hydroxy-but-2-enoicacid-(-4-trifluoromethylphenyl)-amide.

IR (cm$^{-1}$): 3302.1, 2220.3, 1918.4, 1641.2, 1596.7, 1551.7, 1410.3, 1325.6, 1158.4, 1069.8, 969.2, 840.5 and 683.6. The IR of crystalline form of (Z)-2-Cyano-3-hydroxy-but-2-enoicacid-(-4-trifluoromethylphenyl)-amide is shown in FIG. 7.

Comparative data of yield and purity of the final product Teriflunomide and prior art cited in the table.
Formula (I) Teriflunomide

|  | Yield | Purity |
|---|---|---|
| Teriflunomide obtained through the process of the Present Invention | Overall yield: 76.68% (Example 10) | Purity: >99.9% AUC (Example 10) |
| Teriflunomide obtained through process of WO2015/029063 | Overall yield: 55.6% (Example: 2, 3 and 4) | Purity: >99.9% AUC (Example 4) |

The invention claimed is:

1. A process for the preparation of (Z)-2-cyano-3-hydroxy-but-2-enoic acid-(4-trifluoro methylphenyl)-amide of formula-I, comprising the steps of:
a) converting 5-methylisoxazole-4-carboxylic acid of formula-V to 5-methylisoxazole-4-carbonyl chloride of formula-IV using a chlorinating agent;

b) reacting the compound of formula-IV with 4-(trifluoromethyl) aniline of formula-III in a biphasic medium in the presence of an inorganic base to afford N-(4'-trifluoromethylphenyl)-5-methylisoxazole-4-carboxamide of formula-II; and c) reacting the compound of formula-II with aqueous sodium hydroxide in a mixture of solvents to provide (Z)-2-cyano-3-hydroxy-but-2-enoic acid-(4-trifluoromethyl phenyl)-amide of formula-I.

2. The process according to the claim 1, wherein chlorinating agent used in step a) is selected from thionyl chloride, oxalyl chloride, phosphorous oxychloride or phosphorous pentachloride.

3. The process according to the claim 1, wherein inorganic base used in step b) is selected from sodium carbonate, potassium carbonate, sodium hydroxide or cesium carbonate.

4. The process according to the claim 1, wherein biphasic medium used in step b) is selected from ethyl acetate, ethyl methyl ketone, methyl isobutyl ketone, 2-methyl tetrahydrofuran and water.

5. The process according to the claim 1, wherein in step b) the compound of formula II stays in organic layer, preferably in methyl ethyl ketone layer.

6. The process according to the claim 5, wherein the compound of formula II in methyl ethyl ketone is carried forward to step c) with or without separation of aqueous layer.

7. The process according to the claim 1, wherein mixture of solvents used in step c) is selected from methyl ethyl ketone, methanol, methyl isobutyl ketone, 2-methyl tetrahydrofuran, ethyl acetate and water.

8. The process according to the claim 1, wherein mixture of solvents used in step d) is selected from acetonitrile-water, methanol-water and ethanol-water.

9. A process for the preparation of (Z)-2-cyano-3-hydroxy-but-2-enoic acid-(4-trifluoro methylphenyl)-amide of formula-I, comprising the steps of:
a) converting 5-methylisoxazole-4-carboxylic acid of formula-V (V)

to 5-methylisoxazole-4-carbonyl chloride of formula-IV (IV)

using a chlorinating agent with an aromatic hydrocarbon solvent;
b) reacting the compound of formula-IV with 4-(trifluoromethyl)aniline of formula-III (III)

in a biphasic medium in the presence of an inorganic base to afford N-(4'-trifluoromethylphenyl)-5-methylisoxazole-4-carboxamide of formula-II;

(II)

c) reacting the compound of formula-II with aqueous sodium hydroxide in a mixture of solvents to provide (Z)-2-cyano-3-hydroxy-but-2-enoic acid-(4-trifluoromethyl phenyl)-amide of formula-I, wherein step c) reaction is carried on without isolating compound of Formula II;
d) optionally, purifying the compound of formula-I from a mixture of solvents to provide pure crystalline (Z)-2-cyano-3-hydroxy-but-2-enoic acid-(4-trifluoromethyl phenyl)-amide of formula-I.

10. The process according to the claim 9, wherein aromatic hydrocarbon solvent used in step a) is selected from toluene, benzene and xylene.

11. The process according to the claim 10, wherein aromatic hydrocarbon solvent used in step a) is toluene.

12. The process according to the claim 9, wherein chlorinating agent used in step a) is selected from thionyl chloride, oxalyl chloride, phosphorous oxychloride and phosphorous pentachloride.

13. The process according to the claim 9, wherein inorganic base used in step b) is selected from sodium carbonate, potassium carbonate and cesium carbonate.

14. The process according to the claim 9, wherein organic solvent used in step b) is selected from ethyl acetate and ethyl methyl ketone.

15. The process according to the claim 9, wherein mixture of solvents used in step c) is selected from methyl ethyl ketone, methanol, methyl isobutyl ketone, 2-methyl tetrahydrofuran, ethyl acetate and water.

16. The process according to the claim 15, wherein mixture of solvents used in step c) is selected from methyl ethyl ketone, methanol and water.

17. The process according to the claim 9, wherein mixture of solvents used in step d) is selected from acetonitrile-water and methanol-water.

18. A process for the preparation of (Z)-2-cyano-3-hydroxy-but-2-enoic acid-(4-trifluoro methylphenyl)-amide of formula-I (I)

comprising the steps of:
a) converting 5-methylisoxazole-4-carboxylic acid of formula-V (V)

to 5-methylisoxazole-4-carbonyl chloride of formula-IV (IV)

using thionyl chloride in toluene;
b) reacting the compound of formula-IV with 4-(trifluoromethyl)aniline of formula-III (III)

In ethyl methyl ketone and water in the presence of cesium carbonate to afford N-(4'-trifluoromethylphenyl)-5-methylisoxazole-4-carboxamide of formula-II;

(II)

c) reacting the compound of formula-II with aqueous sodium hydroxide in a mixture of methyl ethyl ketone and methanol to provide (Z)-2-cyano-3-hydroxy-but-2-enoic acid-(4-trifluoromethyl phenyl)-amide of formula-I;

d) optionally, purifying the compound of formula-I from a mixture of acetonitrile and water to provide pure crystalline (Z)-2-cyano-3-hydroxy-but-2-enoic acid-(4-trifluoromethyl phenyl)-amide of formula-I.

19. The process of claim 1, further comprising purification of (Z)-2-cyano-3-hydroxy-but-2-enoic acid-(4-trifluoro methylphenyl)-amide of formula-I, wherein said purification comprises the steps of;

i. diluting the crude Formula-I with a mixture of acetonitrile and water;
ii. heating the slurry;
iii. stirring the slurry at hot condition;
iv. cooling the slurry;
v. stirring the slurry;
vi. filtering the solid and washing with acetonitrile; and
vii. drying the solid to get pure Formula-I.

\* \* \* \* \*